United States Patent
Masao

[11] Patent Number: 5,910,841
[45] Date of Patent: Jun. 8, 1999

[54] ELLIPSOMETER USING AN EXPANDED BEAM

[76] Inventor: Katsuya Masao, 7190 103, 4-9-24 Nishikicho, Takikawashi, Tokyo, Japan

[21] Appl. No.: 07/978,223

[22] Filed: Nov. 19, 1992

[30] Foreign Application Priority Data

Nov. 19, 1991 [JP] Japan ............................ 3-354188

[51] Int. Cl.⁶ .................................................. G01J 4/04
[52] U.S. Cl. .......................................................... 356/369
[58] Field of Search ............................ 356/364, 365, 356/366, 367, 369; 250/225

[56] References Cited

U.S. PATENT DOCUMENTS

| | | | |
|---|---|---|---|
| 3,992,571 | 11/1976 | Garlick et al. | 356/365 |
| 4,516,855 | 5/1985 | Korth | 356/369 |
| 4,724,479 | 2/1988 | Schmalfuss et al. | 356/369 |
| 5,076,696 | 12/1991 | Cohn et al. | 356/369 |

*Primary Examiner*—Richard A. Rosenberger
*Attorney, Agent, or Firm*—Armstrong, Westerman, Hattori, McLeland & Naughton

[57] ABSTRACT

An ellipsometer using an expanded beam for measuring characteristic of a sample comprising a beam expander disposed in an incident light beam for expanding the incident light beam, the expanded light beam being reflected from the sample, a condenser lens disposed in the expanded and reflected light beam for condensing the expanded and reflected light beam into a light beam having a cross section, and a photo sensor for receiving the light beam, the cross section of the light beam having a sufficient area for the photo sensor to form a two-dimentional image from the light beam from the condenser lens, whereby the measurement of the elliptically polarized state can be measured at high speed.

10 Claims, 5 Drawing Sheets

ELLIPSOMETER USING AN EXPANDED BEAM

BACKGROUND OF THE INVENTION (1) Field of the Invention

The present invention relates to an ellipsometer using an expaed beam, and more particularly to an ellipsometer which can measure the thickness and a refractive index of a film such as an oxide film on a semiconductor substrate at a high speed and with a low error rate.

(2) Description of the Related Art

As a prior art of an ellipsometer, an automatic ellipsometer invented by Frederic H. Dill et. al, described in U.S. Pat. No. 3,880,524 issued on Apr. 29, 1975, is known. In this prior art, to measure one point on a sample, the state of polarization of light is measured by rotating, mechanically or electrically, and azimuthal angle of an analyzer to detect the total amount of transmitted light, thereby the thickness and the refractive index of he sample are measured.

The rotation of the analyzer from zero degree to 360 degree, however, takes a long time of, for example two to three seconds. In addition, during the rotation, if noises are added to the detected light or if the light intensity fluctuates, the detected result is not correct. Further, since only one point of the sample is detected by one measurement, it takes a very long time to measure the whole surface of the sample.

To speed up the measurement, another prior art is known (Japanese Patent Application No. 62-184250) in which a beam splitter is used to divide a reflected light into three, and three light detectors having different azimuthal angles to each other are used to transmit the divided three reflected light beams, to obtain the state of the polarization of the reflected light by measuring the transmitted light amounts.

This prior art also has a disadvantage of low speed detection because the light beam is incident on only one point on the surface of the sample at one measurement.

SUMMARY OF THE INVENTION

Accordingly, an object of the present invention is to provide a new ellipsometer using an expanded beam which can measure the thickness and the refractive index of a sample at a high speed.

Another object of the present invention is to provide the above ellipsometer which can measure the thickness and the refractive index at a high accuracy.

To obtain the above objects, there is provided, according to the present invention, an ellipsometer using an expanded beam for measuring characteristic of a sample comprising a beam expander disposed in an incident light beam for expanding the incident light beam, the expanded light beam being reflected from the sample, a condenser lens disposed in the expanded and reflected light beam for condensing the expanded and reflected light beam into a light beam having a cross section, and a photo sensor for receiving the light beam, the cross section of the light beam having a sufficient area for the photo sensor to form a two-dimentional image from the light beam from the condenser lens, whereby the measurement of the elliptically polarized state can be measured at high speed.

BRIEF DESCRIPTION OF THE DRAWINGS

The above objects, features and other features of the present invention will be more apparent from the following description of the preferred embodiments with reference to the drawings, wherein.

DESCRIPTION OF THE PREFERRED EMBODIMENTS

Figure 1:
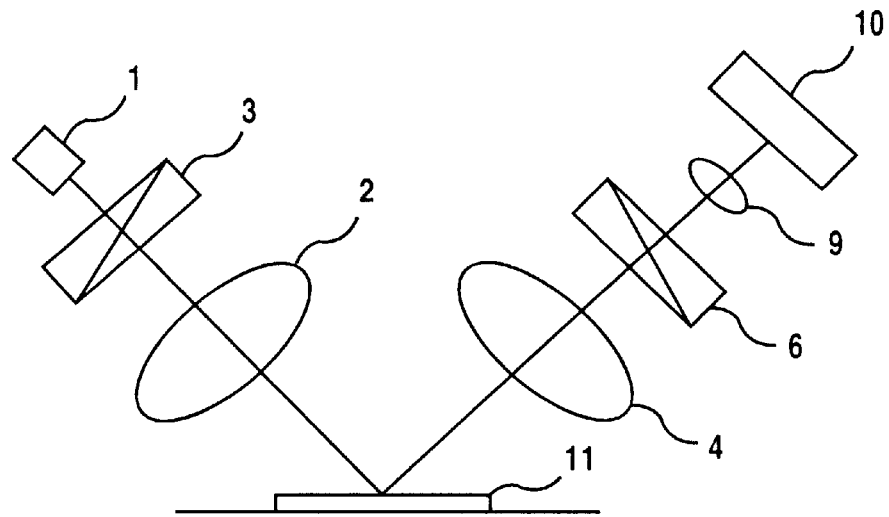
FIG. 1 shows a general construction of an ellipsometer according to a first embodiment of the present invention.

Throughout the description, the same reference numeral represents the same or similar part.

FIG. 1 shows a general construction of an ellipsometer of a first embodiment. In FIG. 1, 1 is a light source such as a laser diode, 2 is a beam expanded, 3 is a polarizer, 4 is a condenser lens, 6 is an analyzer, 9 is an image formation lens, 10 is a photo sensor, and 11 is a sample.

A light beam emitted from the light source 1 passes through the polarizer 3 and is expanded by the beam expander 2 so that an expanded light beam having a certain cross section is incident on the sample 11. Preferably, the expanded light beam is a parallel beam. The expanded parallel beam is reflected from the sample 11 and the reflected expanded beam is condensed to pass through the analyzer and the image forming lens 9 so that a two-dimentional image is formed on the photo sensor 10. It is preferable that the diameter of the expanded light beam is as large as possible as long as the two-dimentional image is formed within the receiving surface of the photo sensor 10.

Preferably, the light beam emitted from the light source 1 has three or more light components having different wave lengths. For example, the light beam is a white light beam consisting of Red, Green, and Blue components. The polarizer 3 converts the light beam from the light source 1 into a linearly polarized light. The linearly polarized light is expanded as above. The expanded parallel light beam is incident on a two-dimentional surface of the sample 11. The reflected beam reflected from the sample 11 is an expanded and elliptically polarized light beam which is then condensed by the condenser lens 4 into light beam having a predetermined cross section. The condensed light beam is then converted into a linearly polarized light by the analyzer 6 and passed through the image forming lens 9. Thus, on the photo sensor 10, the two-dimensional image is formed.

By orientating the polarizer 3 or the analyzer 9 to provide three or more azimuthal angles, and by analyzing the output of the photo sensor 10, the thickness of the film on the sample 11 or the refractive index of the film can be detected at a high speed because the photo sensor 10 receives the expanded light beam. By using the white light, wavelength characteristic of the sample 11 can be detected.

The elliptically polarized state can be expressed by three parameters. Therefore, by detecting the transmitted light amounts by means of three analyzers having azimuthal angles different from each other. Further, by passing the outputs of the three analyzers through three dichroic mirrors, and by detecting the primaries respectively output from the three dichroic mirrors, the light amounts passed through the three analyzers are determined. Thus, the elliptically polarized state can be detected.

When the light source is the one for emitting a which light beam, by forming an image of the light beam on the color area sensor, a two-dimentional distribution of the polarized state in the light beam can be detected. When a color line sensor is used to form an image of the light beam thereon when the light source is the one for emitting a white light beam, a one-dimentional distribution of the polarized state in the light beam can be detected.

The polarized state of the reflected light can be determined so that the thickness and the refractive index of the film can be known By irradiating the surface of the sample with a linearly polarized state light, by transmitting the reflected light through three analyzers having different azimuthal angles, by converting the transmitted lights into three colors, and by measuring the light amounts of respective colors by a color sensor.

Alternatively, by irradiating, on the surface of the sample with an appropriate incident angle, three polarized light beams of three colors having different main axises and colors from each other, by passing the reflected light through an analyzer having a predetermined azimuthal angle, and by measuring the transmitted light amounts of the three colors by a color sensor, the thickness and the refractive index of the film can also be known from the symmetry principle in the optical system.

Alternative to the light beam having three or more different wave lengths, the light source 1 may emit a monochromatic light beam. In this case, the thickness of the film on the sample 11 and the refractive index of the film can be detected but the wavelength characteristic of the sample 11 can not be detected.

In the following various embodiments are described in detail.

Figure 2:
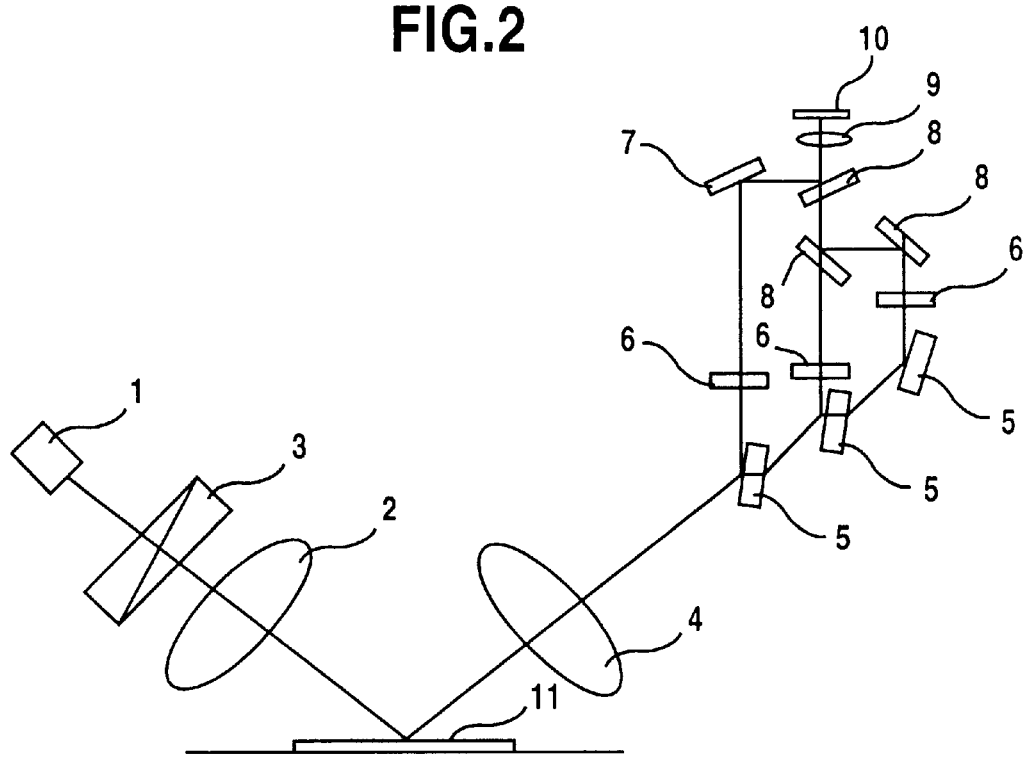
FIG. 2 shows an ellipsometer according to a second embodiment of the present invention.

FIG. 2 shows a second embodiment of the present invention. In FIG. 2, the difference from FIG. 1 is the construction of the optical system between the condenser lens 4 and the photo sensor 10. The condensed light beam passed through the condenser lens 4 is separated by three beam splitters 5 into three light beams. The three light beams are respectively passed through three analyzers 6 having different azimuthal angles and then respectively passed through three dichroic mirrors having different light transmission characteristics. Thus, the polarizations of different azimuthal angles have different colors. These light beams are combined by a total reflection mirror 7 and the image forming lens 9 to be a single light beam so that an image is formed on the color CCD area sensor 10.

The light strengths of the respective colors on the area sensor 10 corresponds to the strengths of the reflected elliptically polarized light corresponding to the azimuthal angles of the analyzers 6.

Figure 3:
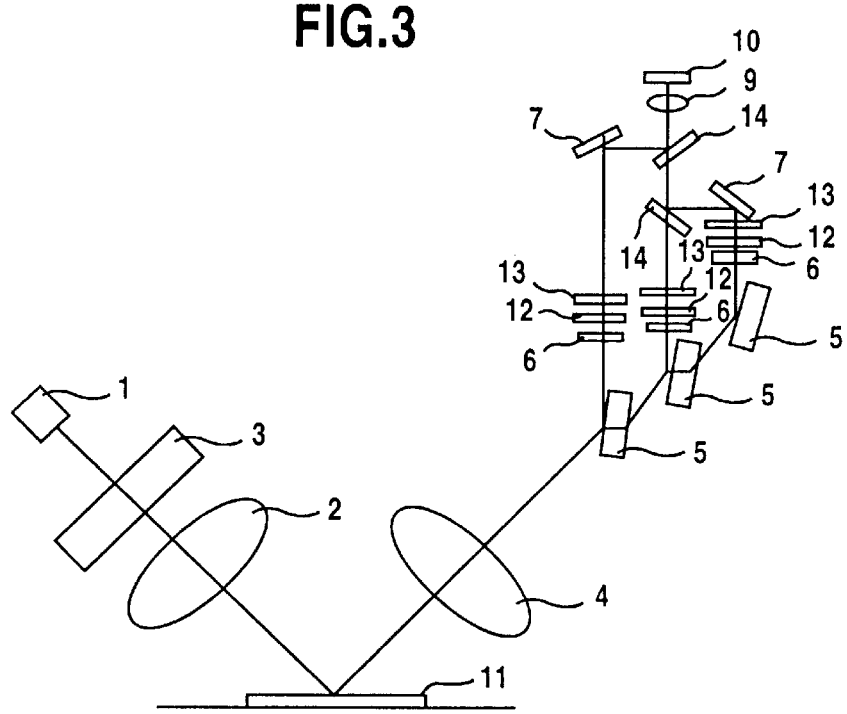
FIG. 3 shows an ellipsometer according to a third embodiment of the present invention.

FIG. 3 shows third embodiment of the present invention. In FIG. 3, the construction is similar to that shown in FIG. 2, and the differences are that the light source 1 emits a light beam of a higher frequency such as an ultraviolet light, and that the optical system between the condenser lens 4 and the sensor 10 is modified from that shown in FIG. 2. Behind the respective analyzers 6, in this embodiment, there are fluorescent plates 12 for absorbing ultraviolet lights to perform a wave length conversion into R, G, and B., and color filters 13 for the R, G, and B for sharpening he emission spectrum. After passing them, the light is formed as a single light beam by the total reflection mirrors 7, and beam splitters 14 so that an image is formed on the CCD color area sensor 10. The light strengths of the respective colors on the area sensor 10 corresponds to the strengths of the reflected elliptically polarized light corresponding to the azimuthal angles of the analyzers 6.

This arrangement does not relate to the detection of the wavelength characteristic of the sample.

Figure 4:
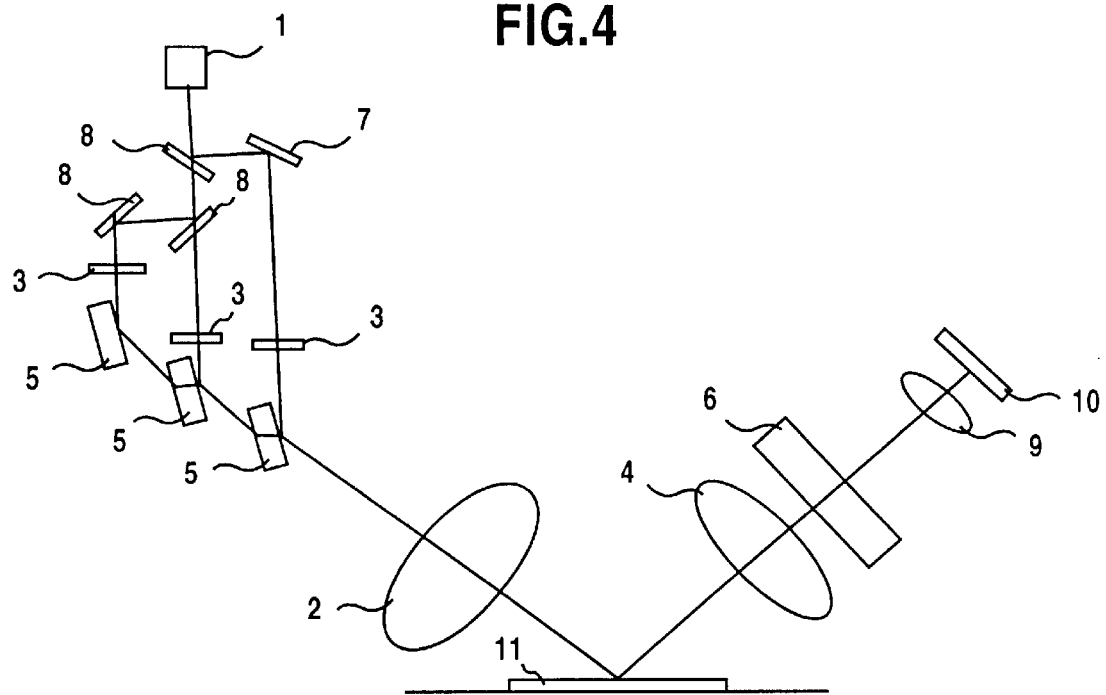
FIG. 4 shows an ellipsometer according to a fourth embodiment of the present invention.

FIG. 4 shows a fourth embodiment of the present invention. The difference between FIG. 1 and FIG. 4 is that, in FIG. 4, between the light source 1 and the beam expander 2 in the incident light path, there are provided the total reflection mirror 7, three dichroic mirrors 8 having different color transmission characteristics, three polarizers 3 having different azimuthal angles, and three beam splitters 5. The total reflection mirror 7 and the dichroic mirrors 8 separates the light beam from the light source 1 into three color components. The azimuthal angles of these polarizers 3 are so selected that the Jones' matrixes are linearly independent from each other. For example, the azimuthal angles may be +45°, 0°, and −45°.

These three light beams from the beam splitters 5 are passed, as one light beam, through the beam expander 2 such as a collimeter lens to be changed into an expanded parallel beam which is then reflected by the sample 11. The optical system in the reflected light path is similar to that shown in FIG. 1.

Let assume that the characteristic matrixes of the sample 11 and the analyzer 6 are (M) and (N), the light strengths of the incident R, G, and B lights are (IRi) (IGi), and (IBi), and the light strengths of the reflected lights R, G, ad B are (IRo), (IGo), and (IBo) respectively. Then, the these are expressed by the following equations:

$(IRo)=(N)\ (M)\ (IRi)$ $(IGo)=(N)\ (M)\ (IGi)$ $(IBo)=(N)\ (M)\ (IBi)$

By normalizing the matrixes with the use of loss coefficients, (M) is an unimodular (2, 2) matrix having two independent parameters. The matrix (M) can be calculated because (N) is a known matrix and the (IRo), (IGo), and (IBo) are obtained from the strengths of the R, G, and B detected by the sensor 10.

The above discussion by using the matrixes can be similarly applied to all of the other embodiments of the present invention.

Figure 5:
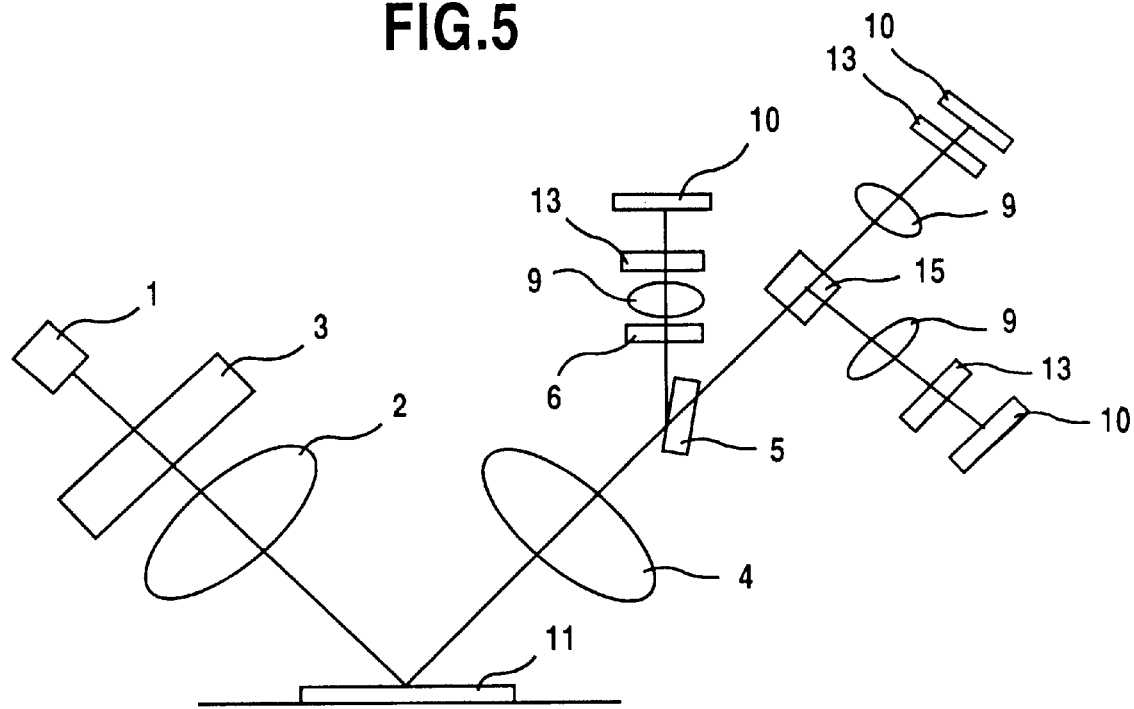
FIG. 5 shows an ellipsometer according to a fifth embodiment of the present invention.

FIG. 5 shows a fifth embodiment of the present invention. The difference between FIG. 1 and FIG. 5 is that, in FIG. 5, an optical syst em different from that in FIG. 1 is provided between the condensing lens 4 and sensors 10. A white light beam or a light beam consisting of the three primaries R, G, and B emitted from the light source 1 passes through the beam expanded such as a collimeter lens 2 to become a linearly polarized light beam which is then incident on the sample 11 with an appropriate incident angle. The reflected light beam passed through the condensing lens 4 and, by a beam splitter 5 and a polarization beam splitter 15, the light beam from the condenser lens 4 is separated into three light beams. The analyzer 6 and the polarization beam splitter 15 have characteristics so that the three light beams are polarized light beams with different azimuthal angles. The three polarized light beams are respectively passed through three image forming lens 9 and three color filters 13 for passing the R, G, and B so that three images are formed on the three color CCD area sensors 10 respectively.

The light strengths of the respective colors on the area sensor s 10 corresponds to the strengths of the reflected elliptically polarized light corresponding to the different azimuthal angles.

Figure 6:
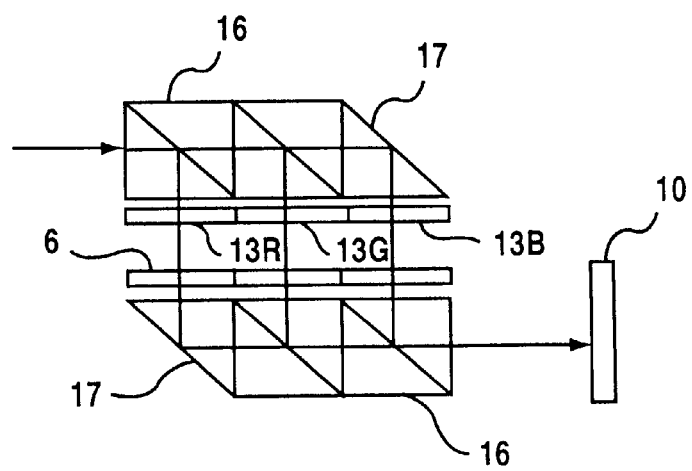
FIG. 6 shows an ellipsometer according to a sixth embodiment of the present invention.

FIG. 6 shows a sixth embodiment of the present invention. In FIG. 6, in stead of the optical system in the reflected light path in FIG. 2, a cubic optical system is employed. As shown in FIG. 6, the light beam reflected from the sample 11 (not shown in FIG. 6 but is the same as that shown in FIG. 2) is separated by a cubic beam splitter 16 and a rectangular prism 17 into three beams which are respectively converted into red, green, and blue beams by color filters 13R, 13G, and 13B. Each of the R, G, B beams is passed through an analyzer 6 so that different combinations of colors and polarized states are obtained. For example, three beams of three combinations (red, +45°), green, 0°), and (blue,−45°) are obtained at the output of the analyzer 6. These beams are superimposed into a single beam by another rectangular prism 17 and another cubic beam splitter 16. To change the combinations of the colors and the polarizes states, the color filters 13R, 13G, and 13B can be replaced with other color filters. For example, at the first time, the combinations are made to be (red, +45°), (green, 0°), and (blue,−45°); at the second time, the combinations are made to be (green, +45°), (blue, 0°), and (red,−45°); and at the third time, the combinations are made to be (blue, +45°), (red, 0°), and (green,−45°). From the three measurement, the change of the polarized states of the red, green, and blue light beams can be detected. It should be noted that, instead of replacing the color filters, it may also be possible to replace the analyzer 6 for obtaining the similar effect.

Figure 7:
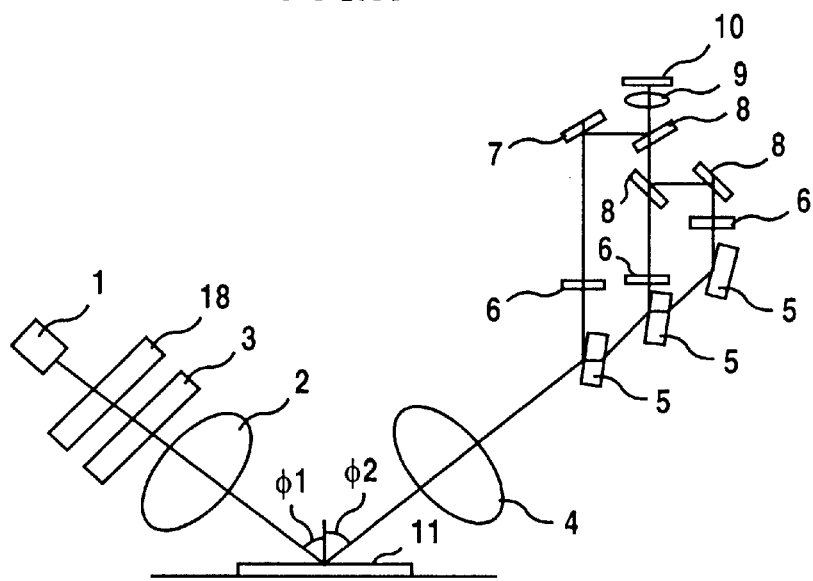
FIG. 7 shows an ellipsometer according to a seventh embodiment of the present invention.

FIG. 7 shows a seventh embodiment of the present invention. FIG. 7 is similar to FIG. 2. The difference between FIG. 2 and FIG. 7 is that, in FIG. 7, a liquid crystal panel 18 is placed between the light source 1 and the polarizer 3. The white light beam emitted from the light source 1 passes through the liquid crystal panel 18, the polarizer 3, and the beam expander 2 to be incident on the sample 11 with an incident angle $\phi 1$. The reflected light beam passes through the condenser lens 4, the beam splitters 5, the analyzers 6, the dichroic mirror 7, the total reflection mirrors 8, and the image forming lens 9 so that an image is formed on the CCD area sensor 10.

By appropriately switching ON or OFF of the picture elements of the liquid crystal panel 18, the continuous incident light beam is changed into an intermittent light beam so that measuring positions on the surface of the sample can be appropriately selected. If the surface of the sample is rough or inclined, the corresponding picture elements of the liquid crystal panel 18 are turned off. By this arrangement, the influence of interference of reflected light beams or displacement of the reflected light beams on the measured results can be prevented.

From the position of he picture element of the liquid crystal panel and the position of the picture element on the CCD area sensor, the reflection angle $\phi 2$ can be calculated, so that the inclination of the surface of the sample 11 at any position can be calculated at $(\phi 2-\phi 1)/2$.

In the above embodiments described with reference to FIGS. 2 to 7, the light source 1 emits a white light beam or a beam consisting of three primaries $R_,$, G, and B. Different from these embodiments, the following embodiments relates to ellipsometers using monochromatic light beams.

Figure 8:
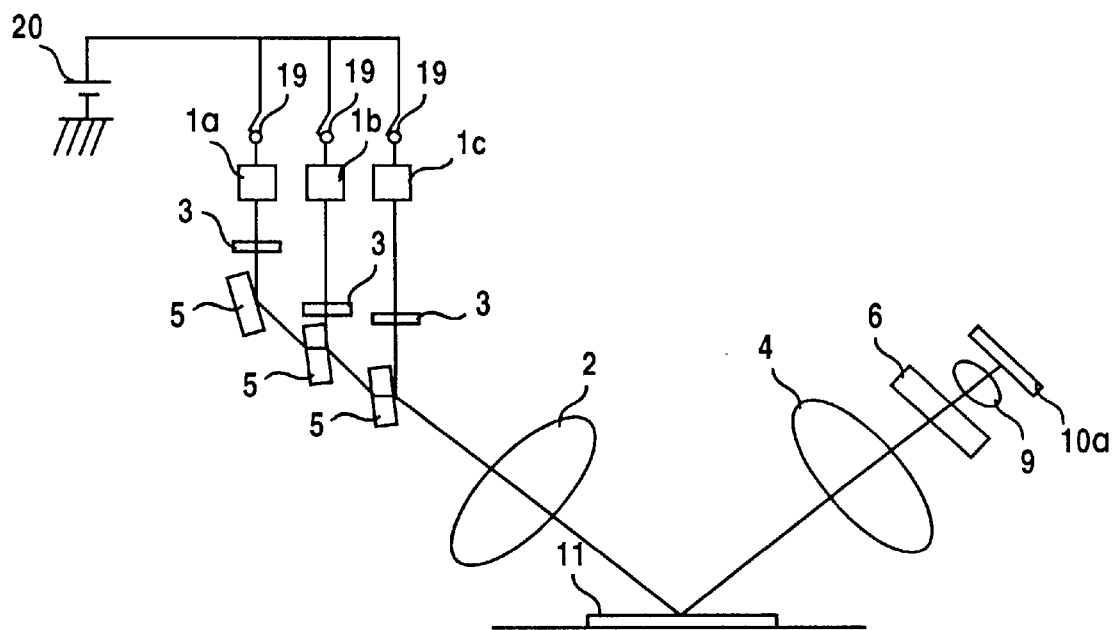
FIG. 8 shows an ellipsometer according to a eighth embodiment of the present invention.

FIG. 8 shows an eights embodiment of the present invention. In FIG. 8, in the incident light path, there is provided an optical system including power supply 20, three switches 19, three monochromatic light sources 1a, 1b, and 1c which can be switches at a high speed such as laser diodes, three polarizers 3, and three beam splitters 5. In the reflected light path, monochromatic sensor 10a is provided. The other elements are the same as those in the already described embodiments.

The three monochromatic light beams emitted from the monochromatic light sources 1a, 1b, and 1c are passed through three polarizers 3 having different azimuthal angles. The power source 20 is controlled by the three switches to that only one light source is turned on at a time.

The transmitting direction of each light beam is adjusted by the corresponding splitter 5 so that the three light beam after passing through the beam splitters 5 are transmitted on the same light path.

The light beam from the beam splitters 5 is expanded by the beam expander 2. Thus, an expanded and parallel light beam is incident on the sample 11.

The reflected light beam is passed through the condensing lens 4 and the analyzer 6 in which the light beam is converted into a linearly polarized light beam. Then, it is passed through the image forming lens 9 so that an image is formed on the area sensor 10a.

It is desirable to sequentially turn the switches 19 in such a way that only one light source is turned on while the area sensor 10a is scanning one frame to read the reflected picture image. Namely, by scanning three frames of the area sensor 10a, the light strengths corresponding to three azimuthal angles of incident polarized lights can be obtained.

The wavelengths of the lights from the three light sources 1a, 1b, and 1c must be the same. Alternatively, when the wavelength characteristic of the refractive index of the film of the sample is known, the wavelengths of the lights from three light sources may be different from each other. In this case, the sensor 10a is preferably a color sensor.

It is possible to know the wavelength characteristic of the refractive index of the film of the sample by using the light sources for emitting lights of different wavelengths and by performing the measurements by changing the combinations of the light sources and the azimuthal angles of the polarizers three times.

Figure 9:
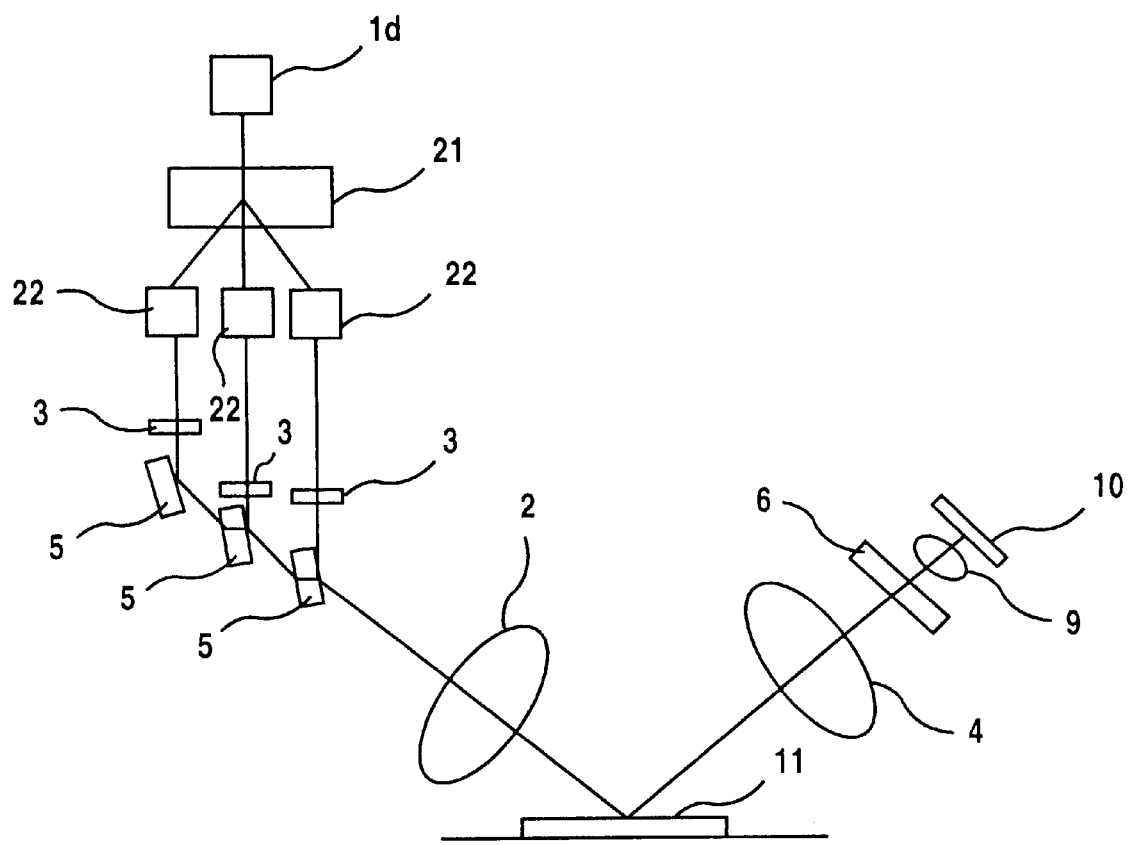
FIG. 9 shows an ellipsometer according to a ninth embodiment of the present invention.

FIG. 9 shows a ninth embodiment of the present invention. The difference between FIG. 8 and FIG. 9 is that, in FIG. 9, instead of the power supply 20, the switches 19, and the light sources 1a, 1b, and 1c, a single monochromatic light source 1d, an optical switch 21, and three mirrors 22 are employed. By this construction, since a single light source is used, the measurement accuracy is higher than that by the ellipsometer shown in FIG. 8.

From the foregoing description it is apparent that, according to the present invention, a new ellipsometer is provided by which the polarized state of light beam can be detected at a high speed and accordingly the thickness and the refractive index of a film can be detected at high speed. In addition, by using a white light beam or a light beam consisting of three primaries, the frequency characteristic of the film for each color component can be detected.

What is claimed is:

1. A ellipsometer for measuring characteristics of a sample by irradiating a polarized light beam on said sample and by analyzing the reflected light beam from said sample, comprising:

a polarizer for converting a light beam from a light source into a polarized light beam;

a beam expander receiving said polarized light beam from said polarizer, for expanding said polarized light beam to form an expanded and polarized parallel light beam having a cross section with a diameter greater than the size of said polarizer, said expanded and polarized parallel light beam being reflected from said sample;

a condenser lens disposed in the expanded and reflected polarized parallel light beam for condensing said expanded and reflected polarized light beam into a condensed light beam having a cross section;

an analyzer receiving said condensed light beam from said condenser lens, for converting said condensed light beam from said condenser lens into a polarized light beam, said cross section of said condensed light beam having a diameter smaller than the size of said analyzer; and a photo sensor for receiving said polarized light beam from said analyzer to detect an image of said sample, wherein said light beam from said light source consists of three components having different wavelengths;

said polarizer is arranged to provide three or more different azimuthal angles of polarized light;

said polarized light beam from said analyzer is a linearly polarized light beam; and an image forming lens is disposed between said analyzer and said photo sensor, for forming, from said linearly polarized light beam, an image on said photo sensor.

2. An ellipsometer as claimed in claim 1, wherein said photo sensor is an area color photo sensor.

3. An ellipsometer as claimed in claim 1, wherein said photo sensor is a line photo color sensor.

4. An ellipsometer as claimed in claim 3, wherein said polarizer is fixedly arranged to provide three different azimuthal angles of polarized lights.

5. An ellipsometer as claimed in claim 1, wherein said polarizer is rotated continuously to provide continuously changing polarizations.

6. An ellipsometer for measuring characteristics of a sample by irradiating a polarized light beam on said sample and by analyzing the reflected light beam from said sample, comprising:

a polarizer for converting a light beam from a light source into a polarized light beam;

a beam expander receiving said polarized light beam from said polarizer, for expanding said polarized light beam to form an expanded and polarized parallel light beam having a cross section with a diameter greater than the size of said polarizer, said expanded and polarized parallel light beam being reflected from said sample;

a condenser lens disposed in the expanded and reflected polarized parallel light beam for condensing said expanded and reflected polarized light beam into a condensed light beam having a cross section;

an analyzer receiving said condensed light beam from said condenser lens, for converting said condensed light beam from said condenser lens into a polarized light beam, said cross section of said condensed light beam having a diameter smaller than the size of said analyzer; and a photo sensor for receiving said polarized light beam from said analyzer to detect an image of said sample, wherein said light beam from said light source consists of three components having different wavelengths;

said polarized light beam from said analyzer is a linearly polarized light beam;

said analyzer is arranged to provide three or more different azimuthal angles of polarized lights; and an image forming lens is disposed between said analyzer and said photo sensor, for forming, from said polarized light beam from said analyzer, an image on said photo sensor.

7. An ellipsometer as claimed in claim 6, wherein said analyzer is rotated continuously to provide continuously changing polarizations.

8. An ellipsometer as claimed in claim 6, wherein said analyzer is fixed at three different azimuthal angles of polarized lights.

9. A ellipsometer using an expanded beam for measuring characteristics of a sample, comprising:

light source for emitting light beam which include three color components;

three polarizers receiving said three color components respectively from said beam separating means for converting said three color components into polarized light beams, said three polarizers being arranged to provide polarized lights of three or more different azimuthal angles;

beam combining means for combining said polarized lights to form a single output beam;

a beam expander receiving said single output beam from said beam combining means, for expanding said single output beam, said expanded output beam being reflected from said sample;

a condenser lens disposed in the expanded and reflected beam for condensing said expanded and reflected polarized light beam into a condensed light beam having a cross section;

an analyzer receiving said condensed light beam from said condenser lens, for converting said condensed light beam from said condenser lens into a linearly polarized light beam;

an image forming lens receiving said linearly polarized light from said analyzer, for forming an image from said linearly polarized light beam; and a color photo sensor disposed to detect said image formed by said image forming lens, said image having a sufficient area for said color photo sensor to simultaneously detect a two-dimensional image which includes said three color components.

10. An ellipsometer using an expanded beam for measuring characteristics of a sample, comprising:

a light source for emitting a light beam which includes three color components;

a polarizer receiving said light beam from said light source for converting said light beam into a polarized light beam, said polarizer being arranged to provide three or more different azimuthal angles of polarized lights;

a beam expander receiving said polarized light beam from said polarizer, for expanding said polarized light beam to form an expanded polarized light beam, said expanded polarized light beam being reflected from said sample;

a condenser lens disposed in the expanded and reflected polarized light beam for condensing said expanded and reflected polarized light beam into a condensed light beam having a cross section;

an analyzer receiving said condensed light beam from said condenser lens, for converting said condensed light beam from said condenser lens into three linearly polarized light beams by color following different paths;

combining means for combining said three linearly polarized light beams to form a single output beam;

an image forming lens receiving said single output beam from said combining means, for forming an image from said single output beam; and a color photo sensor disposed to detect said image formed by said image forming lens, said image having a sufficient area for said color photo sensor to simultaneously detect a two-dimensional image which includes said three color components.

* * * * *